United States Patent [19]
Anderson et al.

[11] Patent Number: 6,129,723
[45] Date of Patent: *Oct. 10, 2000

[54] APPARATUS AND METHODS FOR LASER-INDUCED SUPERFICIAL ALTERATION OF A SUBSTRATE

[75] Inventors: R. Rox Anderson, Lexington; Yacov Domankevitz, Brookline, both of Mass.

[73] Assignee: The General Hospital Corporation, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/563,556

[22] Filed: Nov. 28, 1995

Related U.S. Application Data

[63] Continuation of application No. 08/175,779, Dec. 30, 1993, abandoned.

[51] Int. Cl.[7] .................................................. A61N 5/06
[52] U.S. Cl. ............................. 606/13; 606/2; 606/5; 606/10; 606/17
[58] Field of Search ... 606/2, 3–18; 219/121.6–121.85; 250/505.1

[56] References Cited

U.S. PATENT DOCUMENTS

| | | | |
|---|---|---|---|
| 4,122,342 | 10/1978 | Vali et al. | 250/505.1 |
| 4,273,127 | 6/1981 | Auth et al. . | |
| 4,387,954 | 6/1983 | Beasley | 350/96.15 |
| 4,400,056 | 8/1983 | Cielo | 350/96.19 |
| 4,447,546 | 5/1984 | Hirschfeld | 436/527 |
| 4,585,298 | 4/1986 | Mori | 350/94.1 |
| 4,660,925 | 4/1987 | McCaughan, Jr. | 350/96.15 |
| 4,672,961 | 6/1987 | Davies | 606/7 |
| 4,707,201 | 11/1987 | Failes | 156/64 |
| 4,712,543 | 12/1987 | Baron | 606/5 |
| 4,799,479 | 1/1989 | Spears | 128/303.1 |
| 4,852,567 | 8/1989 | Sinofsky | 606/7 |
| 5,042,980 | 8/1991 | Baker et al. | 606/7 |
| 5,122,060 | 6/1992 | Vassiliadis et al. | 433/215 |
| 5,207,669 | 5/1993 | Baker et al. | 606/7 |
| 5,248,311 | 9/1993 | Black et al. | 606/15 |
| 5,254,114 | 10/1993 | Reed, Jr. et al. . | |
| 5,342,352 | 8/1994 | Franken et al. . | |

FOREIGN PATENT DOCUMENTS

| | | |
|---|---|---|
| 0 400 802 A2 | 12/1990 | European Pat. Off. . |
| 2 154 761 | 9/1985 | United Kingdom . |
| 2 222 881 | 3/1990 | United Kingdom . |
| 9102562 | 3/1991 | WIPO ... 606/17 |

OTHER PUBLICATIONS

Cox et al., "New method for exposing mammalian cells to intense laser radiation using the evanescent . . . ", Med. Phys., 5:274–279 (1978).

Primary Examiner—David M. Shay
Attorney, Agent, or Firm—Fish & Richardson P.C.

[57] ABSTRACT

An apparatus and method for superficially ablating and/or photochemically altering a substrate, e.g., a biological tissue, having a first refractive index, e.g., to a desired configuration, including a laser energy source which provides laser energy to an energy coupling wave generator which generates laser energy waves from the laser energy, the generator having a surface adapted to contact and form an interface with the substrate and having a second refractive index higher than the first refractive index, wherein laser energy entering the wave generator impinges on the surface at an angle of incidence greater than or equal to a critical angle for total internal reflection when the surface is not contacting the substrate, and wherein the wave generator couples the laser energy waves, e.g., refracted or evanescent waves, into the substrate at the interface to superficially ablate the substrate when contacting the substrate.

15 Claims, 3 Drawing Sheets

APPARATUS AND METHODS FOR LASER-INDUCED SUPERFICIAL ALTERATION OF A SUBSTRATE

This is a continuation of application Ser. No. 08/175,779, filed Dec. 30, 1993, now abandoned.

This invention was made with Government support under Contract N00014-86-K-00117 awarded by the Department of the Navy. The Government has certain rights in the invention.

BACKGROUND OF THE INVENTION

This invention relates to the use of electromagnetic wave energy to superficially alter a substrate, e.g., by ablation and/or photochemical reaction.

Lasers are useful in medical, materials processing, and other applications to cause ablation, i.e., substance removal, within a substrate, e.g., biological tissue or other material. In addition, certain lasers, e.g., ultraviolet (UV) lasers, can be used to cause photochemical alterations, e.g., polymerization, in a substrate, with or without simultaneous ablation.

Ablation of biological tissue by lasers occurs predominantly by the rapid thermal vaporization of tissue water. However, secondary processes may coexist with this thermal vaporization. For example, explosive mechanical removal is caused by short laser pulses when laser energy intensity is high enough to initiate a plasma that produces shock waves and mechanical fracture, e.g., greater than about $10^8$ W/cm$^2$. Additionally, UV pulsed laser ablation can cause concurrent photochemical reactions in tissue. When present, these secondary processes can change the efficiency of pulsed laser ablation.

The ablation depth within tissue or other materials depends upon the depth to which the electromagnetic waves penetrate. For some applications, e.g., treatment of large tumors, deep penetration is required, and appropriate wavelength regions, e.g., red or near infrared, are preferable. For other applications, a well-controlled superficial effect is desired, e.g., ablation of the outer surface of the cornea to correct vision, or of the inner surface of diseased arteries.

Laser energy is typically delivered as a beam or illumination in which the electromagnetic energy propagates directly into the tissue or other substrate. Laser energy may also be delivered in the form of refracted or evanescent fields or waves generated at interfaces between two materials that have different refractive indices. For example, evanescent waves have been used in the technique of attenuated total-reflection (ATR) spectroscopy for absorption spectrophotometry, which is a non-destructive measurement tool.

U.S. Pat. Nos. 5,042,980 (corresponding to European Patent Application No. 400,802) and 5,207,669 describe an optical fiber diffusion tip and the use of evanescent waves to direct laser radiation from an optical fiber, e.g., within an angioplasty balloon outwardly through a portion of the balloon surface to heat the tissue surrounding the balloon. The evanescent waves are generated at an interface between the optical fiber and a cladding material of lower refractive index, which is standard in clad optical fibers.

Ablation has been achieved with laser beams by choosing wavelengths that are strongly absorbed by proteins (far ultraviolet radiation, i.e., 193 nm excimer laser) or water (mid-infrared radiation, i.e., 2.9 $\mu$m Q-switched erbium:YAG lasers). In general, the removal of tissue with such strongly-absorbed wavelengths is controlled due to the small "bites" taken with each pulse. This approach also produces the least thermal trauma to surrounding tissue, and creates the smallest-size ablation debris. The relationships between depth of penetration, optical absorption, and pulse duration in determining, e.g., thermal injury, bite size, and efficiency, are well described in the literature. See, e.g., Walsh, J. T., et al., *Lasers Surg. Med.,* 8:108–118 (1988).

However, the same strongly-absorbed wavelength regions are exceedingly difficult to deliver through known optical fiber systems. For example, certain laser angioplasty systems use a special pulse-stretched excimer laser at 308 nm. The pulse-stretching is costly, but is necessary for fiber optic delivery. In addition, the 308 nm wavelength causes thermal damage and is associated with high rates of mutagenesis, but is at present the shortest excimer wavelength that is optical fiber-compatible.

In spite of these limitations, there are examples of the use of strongly-absorbed, short-pulsed lasers for ablation. For example, 193 nm excimer lasers have been used for refractive correction of the eye involving reshaping of the corneal surface. See, e.g., Marshall, et al., U.S. Pat. No. 4,941,093. At present, this is accomplished by sophisticated beam-control systems. Moreover, the required laser is complex in comparison to solid-state lasers.

Laser ablation is also used to remove the stratum corneum, the outermost 8 to 15 $\mu$m dead layer of human skin which provides the major chemical diffusion barrier. The use of such ablation to enhance percutaneous transport was developed by Dr. S. Jacques et al. using both 193 nm excimer, and 2940 nm Er:YAG lasers, e.g., as described in U.S. Pat. No. 4,775,361.

Laser ablation has also been used in dental applications, but has been limited, in part, because laser energy at wavelengths capable of adequate fiber transmission propagate deeply into both enamel and dentin layers, causing excessive heating and damage. The preferred lasers for use with conventional delivery devices for dental applications are erbium or hydrogen fluoride (HF) lasers, running at about 3 $\mu$m wavelength, or UV excimer lasers, running in pulsed modes. However, these lasers are not generally fiber-compatible. For example, the only laser presently commercialized for dentistry is a normal-mode Nd:YAG laser, whose application is limited to caries removal, and must be used in combination with conventional drilling procedures.

Furthermore, laser ablation has been used to a limited extent in angioplasty. Ideally, ablation would remove significant amounts of plaque, avoid perforating the arterial wall, and leave a smooth cylindrical lumen internal surface with minimal thermal injury. It is well established that 193 nm excimer laser pulses can produce smooth, microscopically-controlled removal of atherosclerotic plaque in vitro. However, 193 nm excimer laser pulses cannot be delivered effectively through optical fibers, and thus, long-pulse 308 nm excimer laser pulses and later 2 $\mu$m holmium laser pulses have been used. Unfortunately, these wavelengths penetrate too deeply (50 to 400 $\mu$m) into arterial wall tissue to achieve precise ablation, causing large interaction volumes, large vapor cavitation, and tearing, mechanical injury rather than precise, smooth-surface ablation. Known laser angioplasty catheters are forward-shooting devices which are typically passed over a guidewire to avoid perforating the artery, and are used as an adjunct to balloon angioplasty for total occlusions.

SUMMARY OF THE INVENTION

The present invention uses wavelengths of laser energy that normally create deep penetration, ablation, and injury, in a way that produces a superficial alteration of a substrate, with limited alteration or injury to the surrounding area. In particular, the invention features laser energy delivery apparatus and methods that are safer than conventional laser delivery devices, because no beam is allowed to propagate away from the apparatus when it is not contacting the desired substrate. To achieve this result, the invention employs fundamental principles of physical optics in a novel way to generate refracted or evanescent waves to ablate or photochemically alter a substrate, e.g., tissue, by generating these waves directly in the substrate to be altered. The invention generally features the alteration, e.g., by ablation, photochemical reaction, or other change, of essentially any material capable of laser-induced removal or alteration.

The invention features apparatus for laser-induced superficial alteration, e.g., ablation and/or photochemical alteration, of a substrate having a first refractive index ($n_1$), e.g., biological tissue such as atherosclerotic plaque, stratum corneum, corneal tissue, concretion, tooth enamel, or dentin. The apparatus includes a laser energy source, e.g., a holmium, $CO_2$, dye, erbium, or thulium laser, which provides laser energy, e.g., pulsed laser energy at a wavelength of 1.7 to 2.2 μm, 2.7 to 3.2 μm, 10.6 μm, or 420 to 510 nm, to an energy coupling wave generator, which generates laser energy waves from the laser energy. The generator has a surface adapted to contact and form an interface with the substrate and has a second refractive index ($n_2$) higher than the first refractive index, wherein laser energy entering the wave generator impinges on the surface at an angle of incidence greater than or equal to a critical angle for total internal reflection when the surface is not contacting the substrate, and wherein the wave generator couples the laser energy waves into the substrate at the interface to superficially alter the substrate when contacting the substrate.

In preferred embodiments, the surface of the wave generator is complementary to the desired substrate configuration, and the laser-induced alteration is ablation.

When the wave generator is contacting the substrate and laser energy entering the wave generator impinges on the surface of the wave generator at an angle of incidence greater than or equal to the critical angle for total internal reflection, evanescent waves are coupled into the substrate from the surface of the wave generator to superficially alter the substrate. When the wave generator is contacting the substrate and laser energy entering the wave generator impinges on the surface of the wave generator at an angle of incidence less than the critical angle for total internal reflection, refracted waves are coupled into the substrate from the surface of the wave generator to superficially alter the substrate.

In preferred embodiments, the wave generator is an optical resonator made of sapphire, germanium, silicon, diamond, fused silica, or a combination of these materials. This optical resonator may be a cylinder with a curved side wall and proximal and distal mirrored ends, the surface of the resonator that contacts the substrate being a portion of the curved side wall. The laser energy may be coupled to the generator via an optical fiber, or, if in the form of a beam, may also be coupled directly into the generator.

The invention also features apparatus for superficial alteration, e.g., ablation, of endoluminal tissue to a desired, e.g., concave, configuration. These apparatus have a wave generator with a surface, e.g., a convex cylindrical surface, that is adapted to contact and form an interface with the endoluminal tissue when inserted into an endolumen to be superficially altered.

The invention also features apparatus for superficial alteration of corneal tissue to a desired, e.g., convex, configuration. These apparatus have a wave generator having a surface, e.g., concave, that is complementary to a desired corneal configuration and adapted to contact and form an interface with the corneal tissue.

The invention also features apparatus for ablation of tooth tissue to a desired configuration. These apparatus have a wave generator with a surface adapted to contact and form an interface with the tooth tissue.

In addition, the invention features methods of laser-induced superficial alteration, e.g., ablation and/or photochemically alteration, of a substrate with a first refractive index ($n_1$) by (1) contacting the substrate with a wave generator, e.g., made of sapphire, germanium, silicon, diamond, or fused silica, which generates laser energy waves from the laser energy, the generator having a surface adapted to contact and form an interface with the substrate, and having a second refractive index ($n_2$) higher than the first refractive index, wherein laser energy entering the wave generator impinges on the surface at an angle of incidence greater than or equal to a critical angle for total internal reflection when the surface is not contacting the substrate, and wherein the wave generator couples the laser energy waves into the substrate at the interface to superficially alter the substrate when contacting the substrate, and (2) providing laser energy to the generator.

Various laser energy sources, e.g., a holmium, $CO_2$, dye, erbium, or thulium laser, can be used in the methods of the invention to provide laser energy, e.g., pulsed laser energy at a wavelength of 1.7 to 2.2 μm, 2.7 to 3.2 μm, 10.6 μm, or 420 to 510 nm.

The substrate treated by these methods or apparatus may also be a plastic, polymer, gel, a photosensitive coating, or other material that can be ablated by laser energy. To provide laser-induced photochemical alteration of a substrate, UV laser energy may be used, e.g., from an excimer laser.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications and patents mentioned herein are incorporated by reference. In addition, the materials, methods, and examples are illustrative only and not intended to be limiting.

Other features and advantages of the invention will be apparent from the following description of the preferred embodiments thereof, and from the claims.

The drawings are first briefly described.

DETAILED DESCRIPTION

The present invention uses wavelengths of laser energy in a novel way that produces controlled superficial alteration, e.g., ablation and/or photochemical alteration, of a substrate with limited alteration or injury outside the target area. The apparatus of the invention is safer than conventional laser delivery devices because no beam is allowed to propagate away from the device when it is not contacting the desired substrate.

Normal Incident Ablation

In general, thermally-driven ablation or photochemical alteration of a substrate, e.g., biological tissue, in air by normally-incident, well-absorbed short laser pulses may be described by a first-order model which reveals relationships between tissue optical absorption, depth of ablation and thermal injury, and the laser pulse duration and fluence (energy/area) needed for ablation. The normally-incident laser energy is absorbed by the substrate according to Beer's law, i.e., the intensity I(z) inside the substrate decreases exponentially with depth z:

$$I(z) \approx I_o e^{-\mu_a z},$$

where $\mu_a$ is the optical absorption coefficient of the substrate, and $I_o$ is the incident intensity. With the laser energy delivered at normal incidence, the characteristic penetration depth, $\delta$, is given by:

$$\delta = 1/\mu_a,$$

which is the thickness of the layer in which most of the laser energy is absorbed. In this layer, the incoming energy is converted to heat, which immediately begins to diffuse to the surroundings. The most precise, efficient ablation is achieved when the thermal energy is confined to this layer, i.e., when the laser energy is delivered before the time needed for significant cooling of the layer. This concept defines a "short" laser pulse, which is preferred for use in the present invention. A short laser pulse has a pulsewidth, $\tau_p$, less than the thermal relaxation time, $\tau_r$, of the layer in which energy is absorbed ($\tau_p < \tau_r$). The thermal relaxation time, $\tau_r$, is related to heat conduction by:

$$\tau_r \approx \delta^2/\alpha$$

where $\alpha$ is the thermal diffusivity of the tissue (e.g., for endoluminal tissue this value is $1.3 \times 10^{-3}$ cm$^2$/sec). For a normally-incident beam, therefore:

$$\tau_r \approx (\mu_a^2 \alpha)^{-1}$$

The incident fluence, $F_o$ (energy/area), necessary for tissue ablation is given by the requirement that the heat of vaporization for tissue water be delivered at the tissue/device interface by each pulse. The energy absorbed per unit volume, $E_v$, at the interface is given by:

$$E_v = F_o \mu_a$$

Experimental data with a variety of pulsed lasers suggests that tissue ablation requires $E_v \sim 2500$ J/cm$^3$ (similar to vaporization of pure water) such that ablation is reliably achieved when $F_o \sim 2500/\mu_a$.

With each short laser pulse of sufficient incident energy, a layer of approximately $\delta$ in thickness is removed, and a layer of several times $\delta$ remains as thermally-denatured tissue. The thickness of this remaining thermally-denatured tissue is important during wound healing.

This model reveals the primary importance of $\delta$, the optical penetration depth, not only for determining the scale of the tissue layer removed and residual thermal damage, but also for choosing the optimal laser wavelength and pulse-width. For the least thermal damage and best efficiency of ablation, $\tau_p < \tau_r$, and hence in practice the optimal laser pulsewidth $\tau_p$ varies with $\tau_r$. For $\delta \sim 1$ μm and $\alpha = 1.3 \times 10^{-3}$ cm$^2$/sec, $\tau_r$ is about 1 μs.

If tissue ablation is to be carried out with μm scale precision using normally-incident laser pulses, a wavelength must be chosen for which the tissue absorption is high enough, i.e., $\mu_a \sim 10^4$ cm$^{-1}$, such that $\delta = 1/\mu_a$ $10^{-4}$ cm = 1 μm. Such high tissue absorption coefficients are difficult to achieve, and occur only in the far ultraviolet below 220 nm and at the strongest infrared water absorption band at 2.94 μm. Ideally, even greater precision could be obtained if $\delta$ were significantly less than 1 μm.

Radiation Delivered From A Solid Interface

Figure 1A:
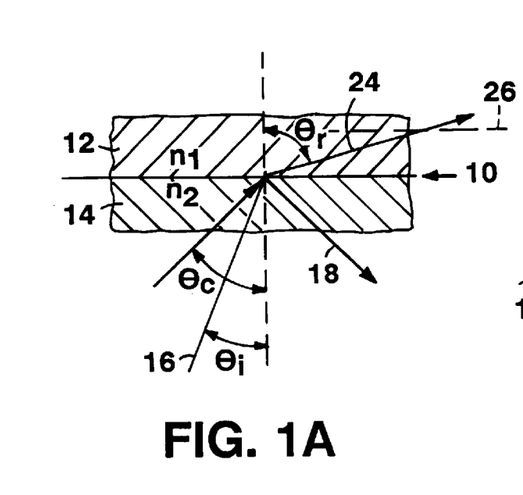
FIGS. 1A and 1B are diagrammatic representations of the physics of wave behavior at an interface between two media of different refractive indices.
Figure 1B:
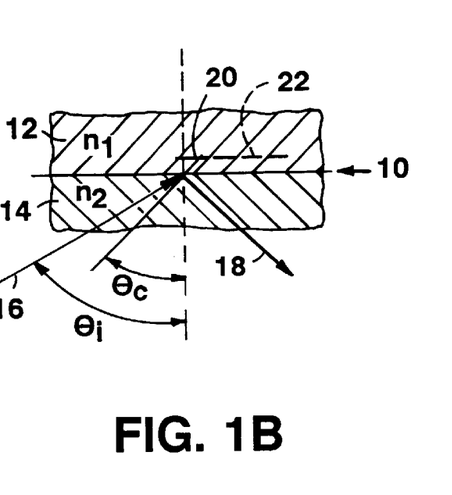

Refraction and reflection at a planar boundary between two media of different refractive index is classically described by Snell's law and Fresnel's equations, which are related to Maxwell's wave equations for electromagnetic radiation at an interface. Referring to FIG. 1A, for refraction from a medium 14 of higher refractive index $n_2$, to a medium 12 of lower refractive index $n_1$, Snell's law states that:

$$n_2 \sin \theta_i = n_1 \sin \theta_r,$$

where $\theta_i$ is the angle of incidence and $\theta_r$ is the angle of refraction. "Total" internal reflection 18 occurs at the interface 10 when the angle of incidence is greater than or equal to a critical angle $\theta_c$ given by $\theta_c = \arcsin n_1/n_2$. This reflection is referred to as "total," because a certain amount of energy is still present in the external medium in a thin layer just past the interface 10. Referring to FIG. 1B, this energy is in the form of a field of evanescent waves 20, which are described in more detail below.

Producing Refracted Waves

As shown in FIG. 1A, the creation of refracted wave 24 in substrate 12, e.g., tissue, requires that laser energy 16 be delivered across interface 10 to tissue 12 with a refractive index $n_1$, from medium 14 of higher refractive index $n_2$, at an angle less than the critical angle, $\theta_c$, for total internal reflection. Under these conditions, the depth of penetration, $\theta_r$, represented by dashed line 26 of laser energy 16 into tissue 12 as a refracted wave 24 is a function of the angle of refraction, $\theta_r$, and the absorption coefficient, $\mu_a$, of the substrate into which the laser energy is transmitted:

$$\delta_r \approx (1/\mu_a) \cos \theta_r$$

The penetration depth is reduced by a factor of $\cos \theta_r$, compared with normally-incident radiation. In practice, this can reduce the penetration depth by up to about one order of magnitude.

Table 1 below shows predicted penetration depth $\delta_r$ for refracted beams from an interface for 2 μm wavelength holmium laser radiation ($\mu_a \approx 50$ cm$^{-1}$ in most tissues). Also shown are the thermal relaxation time, $\tau_r$, assuming a thermal diffusivity for tissue, α, of $1.3 \times 10^{-3}$ cm$^2$/sec, and the approximate minimum depth of residual thermal injury ($\approx 2\delta_r$).

TABLE 1

| angle of refraction ($\theta_r$, degrees) | optical penetration depth ($\delta_r$, μm) | thermal relaxation time ($\tau_r$, seconds) | min. thermal injury depth (μm) |
|---|---|---|---|
| 0 (normal) | 200 | 0.3 | 400 |
| 45 | 140 | 0.15 | 280 |
| 80 | 50 | 0.15 | 280 |
| 85 | 20 | 0.003 | 40 |

It is apparent from Table 1 that a refracted wave generator for holmium laser radiation operating at $\theta_r = 85°$ would reduce the penetration depth, and hence the thermal injury, deposited energy per unit area, and cavitation volume by an order of magnitude compared to a normally incident laser beam. Although this is a large refraction angle, it is well within the capability of both direct and fiber-coupled lasers, because of the low divergence of low numerical aperture fibers. Standard, normal-mode holmium lasers in surgical use operate at pulse durations of 100 to 300 μs, such that $\tau_p < \tau_r$ even for a refracted beam at $\theta_r = 85°$. Thus, a device that produces near-surface refraction can be pumped by existing, normal-mode holmium lasers.

The energy needed for superficial alteration such as ablation by these refracted waves is calculated as follows. At a refractive interface, the incident fluence is given by:

$$F_o = (1-R) F_b \cos \theta_i / \cos \theta_r$$

where R is the Fresnel reflectance from the interface, and $F_b$ is the fluence of the beam from the laser propagating into medium 14. R depends on the indices of the two media, the angle of incidence and the polarization according to Fresnel's equations. As noted above, reliable short-pulse ablation is achieved when $E_v \approx 2500$(J/cm$^3$). R is typically 0.8 to 0.9 for such near-surface refraction, depending on $n_1$. Combining equations and solving for $F_b$ (for ablation), the beam fluence in medium 14, gives:

$$F_{b(ablation)} \approx 2500 \cos \theta_r / [\mu_a (1-R) \cos \theta_i]$$

Refracted waves 24 are produced whenever the angle of incidence $\theta_i$ is less than the critical angle for total internal reflection $\theta_c$. This physical constant is used to construct a refracted wave generator such that it radiates refracted waves into the target substrate to be ablated when the generator interface 10 is contacting the substrate. However, the wave generator is also constructed so that no refracted waves are generated when laser energy 16 is delivered across interface 10 to a medium, e.g., air or water, other than the target substrate. This is achieved by selecting an incidence angle, $\theta_i$, greater than or equal to the critical angle, $\theta_c$, for total internal reflection when the generator is not contacting the target substrate, i.e., when it is air, water, or bodily fluids, depending on the desired use of the device.

For example, the critical angle, $\theta_c$, for a germanium (Ge)/air interface is 14°, and for a Ge/tissue interface is 20°. A Ge rod with the distal end ground and polished at 16° from perpendicular to the central axis will provide an incidence angle, $\theta_i$, of 16°. With this incidence angle, laser energy would be coupled into the tissue as refracted waves because the incidence angle is less than the critical angle for total internal reflection for the Ge/tissue interface, but laser energy would not radiate into air because the incidence angle is greater than the critical angle for total internal reflection for the Ge/air interface.

This is an important safety feature and useful advantage of the invention over present surgical laser delivery devices. No beam is allowed to propagate away from the device when it is not contacting the desired substrate, hence it is unlikely to accidentally ignite materials such as surgical drapes, clothing, etc., or to damage substrate, e.g., healthy tissue, adjacent the target area. Because energy is coupled directly into the substrate, e.g., tissue, only on contact, it is also easier to perform precise surgical ablation.

The present invention also provides another safety benefit that results from a previously undescribed phenomenon that occurs with the ablation of tissues according to the invention, which is essentially absent with normally incident beam delivery. During short laser pulse ablation, vapor cavitation and mechanical injury occur in part because the ablation produces thermal confinement, and causes a sudden increase in temperature and pressure at the site of energy absorption, with super-heating of tissue water during the laser pulse. The vaporization rate of water (and tissue) increases asymptotically as the critical temperature near 320° C. is approached. Thermal expansion occurs, the pressure decreases, and vaporization begins. The onset of vaporization typically requires 0.5 to 2 μs even for high-energy submicrosecond pulses, and vaporization continues long after the pulse has been delivered. When the external medium is air, the vapor expands freely from the tissue surface. However, when the external medium is a fluid or tissue, a rapidly-expanding vapor cavity is formed, which grows and then violently collapses on a micro- to millisecond time scale.

In contrast to free-beam ablation, during which laser energy continues to be delivered during the vaporization and ablation process, as soon as vaporization begins with any superficial refracted wave generator, the tissue is transiently replaced by a growing vapor cavity. Total internal reflection will then occur at the device/tissue interface until the vapor cavity collapses. Thus, the vaporization process at a refractive interface temporarily "turns off" its own energy source, by decoupling transmission through the interface.

This self-limiting feature also occurs in devices for superficially altering substrates located in fluids, where the device is designed not to propagate a refracted wave into the fluid, or air, when not in contact with the substrate.

Refracted waves can be generated in tissue and other substrates using standard optical materials for medium 14. Sapphire is a desirable material for making a practical wave generator because of its high refractive index, broad optical transmittance band, and extreme thermal and mechanical ruggedness. For a sapphire device (n=1.7), to achieve an angle of refraction, $\theta_r$, of 85°, the angle of incidence, $\theta_i$, must be 50°. Setting R=0.9 and $\mu_a \approx 50$ cm$^{-1}$ (tissue absorption coefficient value when using a holmium laser), the beam fluence required for ablation, $F_b$, will be about 67 J/cm², which is only slightly higher than the ablative fluence of 50 J/cm² required for free-beam ablation. Thus, a practical refracted wave generator is relatively efficient.

This may seem paradoxical because R is 0.9, i.e., 90% of the energy incident on the interface is reflected rather than being absorbed. However, as shown in Table 1 above, the energy transmitted through the interface is deposited in a much thinner layer. The order of magnitude "lost" by reflectance is "regained" by the order-of-magnitude decrease in the layer thickness, and hence volume, into which the energy is deposited.

Producing Evanescent Waves

The invention also encompasses the use of evanescent optical wave energy to cause superficial alteration, e.g., ablation or photochemical alteration, in tissue or other material, using wavelengths which at normal incidence could harmfully penetrate deeply into the tissue or material. FIG. 1B shows that evanescent waves 20 exist near the interface 10 between mismatched dielectric media 12, 14. These waves occur when laser energy 16 is delivered across an interface 10 to substrate 12, e.g., tissue, with a refractive index $n_1$, from a medium 14 of higher refractive index $n_2$, at an angle, equal to or exceeding the critical angle, $\theta_c$, for "total" internal reflection.

For "total" internal reflection to occur, destructive interference must occur in the forward direction. The boundary conditions require that the electromagnetic laser energy be present in a thin layer somewhat less than one wavelength thick, on the other side of the interface. Thus, energy is present in the external medium or substrate in a thin layer adjacent to the interface. The waves in this layer are called evanescent waves because they decay rapidly to zero. Under these conditions, laser energy 16 penetrates into substrate 12 as an evanescent wave 20, to a depth of approximately one wavelength or less, represented as dashed line 22, regardless of how deep laser energy at that wavelength would normally penetrate if applied to the tissue directly, e.g., as a free beam.

Evanescent waves are a novel means for limiting penetration depth of laser pulse energy into the external medium or substrate, e.g., tissue. If this substrate sufficiently absorbs the laser energy, the absorbed evanescent wave energy drives interactions covered by this invention, such as tissue ablation or photochemical alteration in a thin layer. The wavelengths of visible and near-infrared light are about right for the evanescent wave field to give the desired 0.1 to 1 $\mu$m penetration depth, $\mu_e$.

The following studies have been undertaken to assess the practicality of precise tissue ablation using evanescent wave energy deposition. Maxwell's wave equations in the plane wave approximation for electromagnetic radiation at interfaces between dielectric optical materials and water have been solved, the deposition of energy with depth has been analyzed, a prediction has been made of the requirements for laser pulses to achieve evanescent wave ablation, and the feasibility of ablation within the limits of rugged visible-infrared optical materials such as silica, sapphire, and silicon has been assessed.

An analysis shows that evanescent wave ablation of tissue is possible at the 1.95 $\mu$m water absorption band, in the far-infrared, and for some tissues, in the near-UV. The 1.95 $\mu$m water absorption band is most compatible with fiber-optic transmission of laser pulses.

The evanescent wave field strength, $E_t(x,z,t)$, is given generally by:

$$E_t(x,z,t) = E_t\, e^{i(\omega t - k_x x)} e^{-(\gamma k z)}$$

where $$\gamma = (n_2^2 \sin^2 \theta_i - n_1^2)^{1/2} / n_2 \cos \theta_i$$

and $k_z$ and $k_x$ are wave vectors in the planes perpendicular and parallel to the interface respectively. The power (intensity) is proportional to $E_t^2 e^{-(2\gamma k z)}$. The penetration depth $\delta_e$ of the evanescent wave field is derived from wave theory and is:

$$\delta_e = 1/k_z \gamma = \lambda \cos \theta_i / 2\pi (n_2^2 \sin^2 \theta_i - n_1^2)^{1/2}$$

When the lower refractive index medium, e.g., the target substrate, absorbs energy, the index $n_1$ is replaced by the complex refractive index, $n_1 = n_1 - ik$, where k is an absorption factor defined as: $\lambda \mu_a/4\pi$. This introduces $\mu_a$, the absorption coefficient of the external medium, e.g., tissue, into the above equation, thus allowing the solution of the above equation for the fraction of incoming energy, 1−R, absorbed by the tissue from the evanescent wave field. The absorbed fraction for polarization perpendicular to the plane of incidence is:

$$(1 - R\perp) = 4\gamma_i/(1+\gamma_r^2),$$

and for polarization parallel to the plane of incidence is:

$$(1 - R_=) = 4\gamma_i (n_2/n_1)^2 / [(1+\gamma_r^2)^2 (n_2/n_1)^2]$$

These solutions allow the calculation of the fraction of incident energy absorbed in water, which mimics wet tissue absorption in the infrared spectrum, at different laser wavelengths of interest coming from different optical materials at and beyond the critical angle. These computations were made by substituting known values for $\mu_a$ as a function of wavelength into the above equations, and were used to generate the graphs of FIGS. 2A and 2B, which show the penetration depth in $\mu$m and absorbed fraction, 1−R for unpolarized light, as a function of incidence angle in germanium (Ge), ZnSe, and sapphire ($Al_2O_3$) for $CO_2$ ($\lambda = 10.6$ $\mu$m) and holmium ($\lambda = 2.1$ $\mu$m) lasers.

Figure 2A:
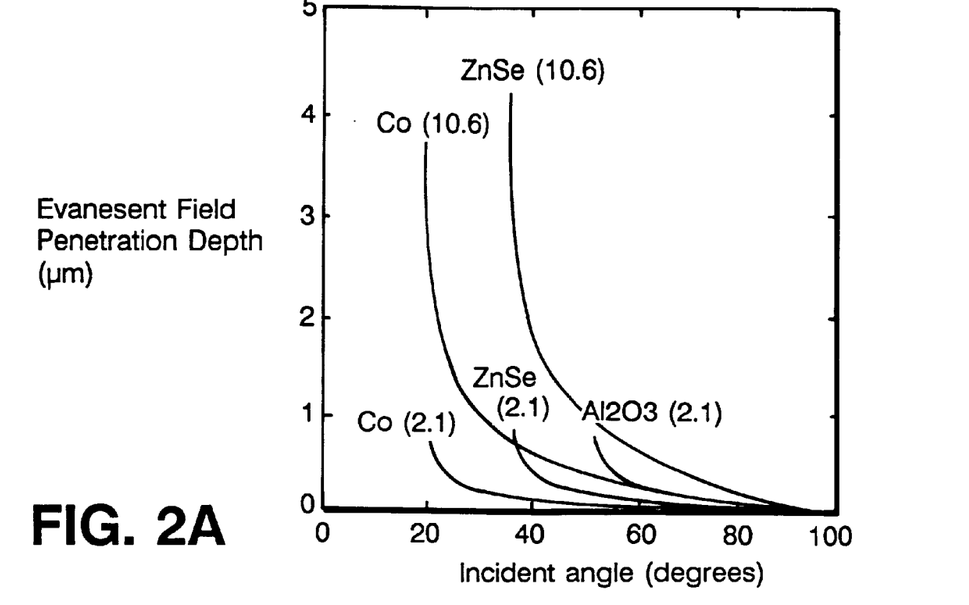
FIG. 2A is a graph of the penetration depth of an evanescent field into tissue as a function of incidence angle.
Figure 2B:
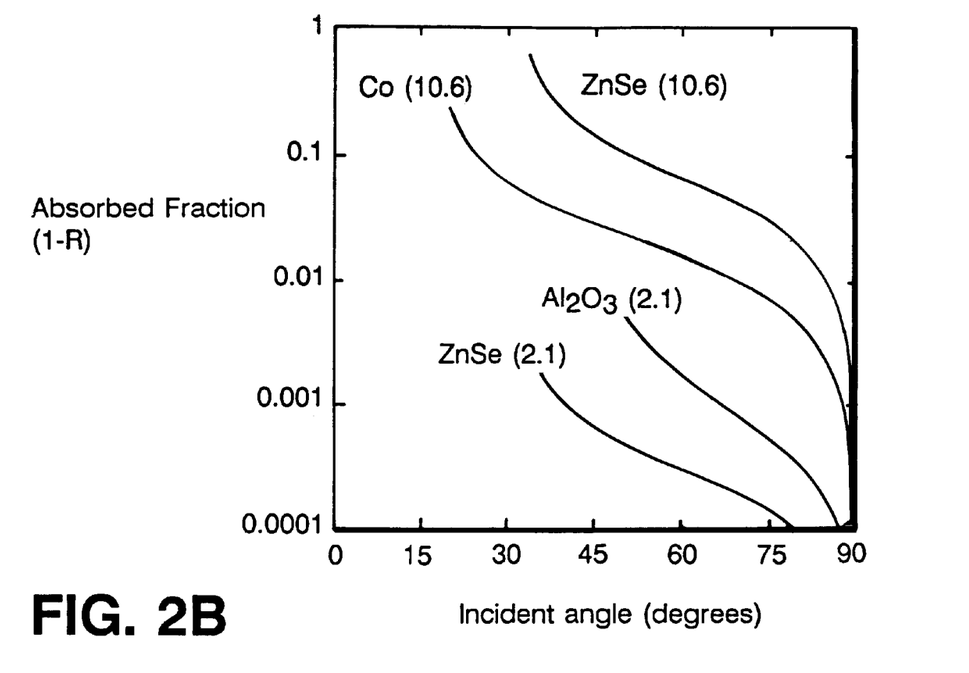
FIG. 2B is a graph of the evanescent wave energy absorbed by tissue as a function of incidence angle.

FIG. 2A allows one to design devices for specific penetration depths by controlling the incident angle. FIG. 2B allows one to calculate the incident fluence necessary to achieve ablation.

Furthermore, Table 2 below lists the fraction of incident energy absorbed by water from the evanescent wave field generated at a sapphire/water interface using a 2.1 $\mu$m wavelength holmium laser ($\mu_a \approx 50$ cm$^{-1}$) with an angle of incidence, $\theta_i$, equal to the critical angle, $\theta_c$. Table 2 also lists the fraction of incident energy absorbed by water from the evanescent wave field generated at a Ge/water interface using a 10.6 $\mu$m wavelength $CO_2$ laser ($\mu_a \approx 1000$ cm$^{-1}$) with $\theta_i = \theta_c$. The penetration depth of the evanescent field, $\delta_e$, predicted incident fluence required for vaporization of water ($F_o$), and the laser pulse duration for thermal confinement within the evanescent field depth, $\tau_r$, are also shown, derived from the equations above.

TABLE 2

Evanescent Wave Ablation Parameters

| Laser (wavelength) | $CO_2$ (10.6 μm) | Holmium (2.1 μm) |
|---|---|---|
| critical angle, $\theta_c$ (material) | 20° (Ge) | 49° (sapphire) |
| Absorbed fraction | 0.237 | 0.00552 |
| normal penetration depth $(1/\mu_a)$ | ≈10 μm | ≈200 μm |
| Evanescent field depth $(\delta_e)$ | ≈3.5 μm | ≈0.5 μm |
| Incident fluence for vaporization $(F_o)$ | ≈3.7 J/cm$^2$ | ≈22 J/cm$^2$ |
| Ideal pulsewidth $(\tau_p \approx \tau_r)$ | ≈100 μs | ≈0.2 μs |
| Laser pulse irradiance for ablation (W/cm$^2$) | 3.7 × 10$^4$ | 1.1 × 10$^8$ |
| Fiber optic damage (W/cm$^2$) | (no fiber) | 2.5 × 10$^8$ |

The practicality of evanescent wave-driven superficial alteration, e.g., ablation, is apparent from the analysis. When a $CO_2$ laser (λ=10.6 μm) is used, the evanescent field deposits over 20% of the incident energy, because of the high value for $\mu_a$ of about 1000 cm$^{-1}$, in a layer only a few μm thick. When a holmium laser is used, which is compatible with fiber optics, and which has a weaker tissue-water absorption band near 2 μm, the absorbed energy from the evanescent field is only about 0.55% of the incident energy. However, as shown in Table 2, ablation should occur below the intensity threshold for fiber optic damage of fused silica (the optical fiber material shown in the table above), silicon, and sapphire.

One way to drive a fiber-coupled evanescent wave generator to achieve tissue ablation is to provide laser energy pulses near wavelength 2 μm with a carefully chosen pulse duration. The pulse duration $\tau_p$ is critical because $\tau_p$ determines the energy intensity a fiber is exposed to for a given laser pulse. The ablation of tissue must be accomplished without damage to the coupling fiber's core, which is an intensity-dependent process. Therefore, a laser is needed at this wavelength range which has both high pulse energy and a pulse-width that can be tuned in the region around 1 μs. One such laser is a cryogenic holmium/thulium laser made by Rare Earth, Inc. (Dennis, Mass.).

Figure 3A:
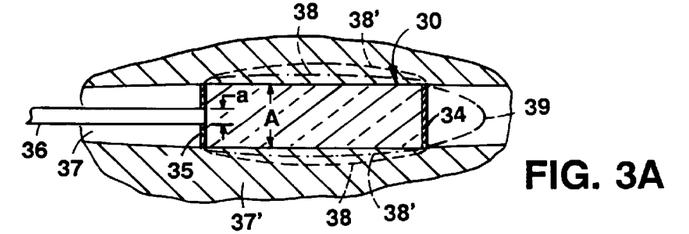
FIG. 3A is a schematic of an optical wave generator intended for use in lumens such as arteries.

Evanescent waves can be generated in tissue and other substrates using standard optical materials, preferably of high refractive index with excellent mechanical properties, for an evanescent wave generator (30 in FIG. 3A, medium 14 in FIG. 1B). In the case of most soft tissue, n=1.35 to 1.38. This is substantially lower than that of fused silica (n=1.5), sapphire (n=1.7), or silicon (n=3.45) at the holmium laser's 2 μm wavelength. In the UV, visible, and near infrared regions, sapphire or fused silica are appropriate materials for the medium 14. In the infrared region, e.g., beyond about 1000 nm, germanium may be used as medium 14 for its very high refraction index (n=4). Other dielectric optical materials such as glasses, polymers, and diamond may also be used for the generator.

Whatever material is used, the device coupling laser energy to the tissue must be designed specifically to create an evanescent wave, by controlling the angle of incidence and/or delivery fiber numerical aperture, such that radiation incident at the device-tissue interface is equal to or greater than the critical angel, $\theta_c$. Many different configurations are possible, depending on the desired application. Specific embodiments are described below.

Refracted Wave and Evanescent Wave Generators

In order to use refracted or evanescent waves, e.g., for angioplasty, a device must be employed that converts the maximum amount of fiber-delivered laser energy into the desired waves, as opposed to the conventional approach of allowing the energy to simply propagate out of the fiber or optical catheter as a free beam. To take the best advantage of refracted and evanescent wave-induced superficial alteration, unique fiber-coupled optical resonators have been devised.

For refracted wave-induced alteration, e.g., ablation, a prism-like wave generator or a refracted optical resonator is constructed to have an internal surface such that the incoming energy hits the surface at an incident angle less than the critical angle for total internal reflection and greater than zero at the device/tissue interface. For evanescent wave-induced alteration, an optical resonator is constructed which has an internal surface such that the incoming energy hits the surface at an incident angle greater than or equal to the critical angle for total internal reflection at the resonator/tissue interface. The use of a resonator, which produces multiple encounters between the radiation and the device's surface, increases efficiency. The resonator type wave generator can also itself be part of the laser cavity, e.g., functioning as a highly-reflective end mirror.

Optical Resonator Ablation Device for Laser Angioplasty and Other Endoluminal Ablation To date, laser recanalization is used mainly to assist access for balloon angioplasty, rather than to create a new round, smooth lumen. Even after a "drilling" laser angioplasty or mechanical angioplasty device is used to gain access, it is necessary to debulk the tissue and to leave a smooth, round surface without perforation of the vessel walls. Specifically, the ideal system would: (1) create a smooth, round lumen of a predetermined size; (2) produce minimal thermal injury to tissue; (3) produce debris smaller than about 7 μm, the size of red blood cells; (4) deliver light directly to the inner walls of vessels; and (5) avoid perforation.

According to the present invention, both refracted and evanescent optical wave ablation can be used to create such a lumen, without excessive tissue injury, and with appropriately small debris size, using fiber-compatible laser wavelengths that when used as a free beam penetrate too deeply and damage otherwise healthy tissue.

As shown in FIG. 3A, an optical resonator 30, situated in a blood vessel 37 within tissue 37', includes opposed mirrors 34, 35 which produce multiple encounters between the laser radiation and the resonator's surface to greatly increase the refracted or evanescent wave field strength, while simultaneously delivering energy to tissue via the desired waves. These waves penetrate tissue 37', with refractive index $n_1$, to a depth of about 20 μm when a holmium laser is used operating at $\theta_r$=85° as discussed above for refracted waves (shown by dashed line 38'), or about one wavelength for evanescent waves (shown by dashed-dotted line 38). In a preferred embodiment, the resonator may be provided with an atraumatic blunt tip (shown by dashed lines 39).

Figure 3B:
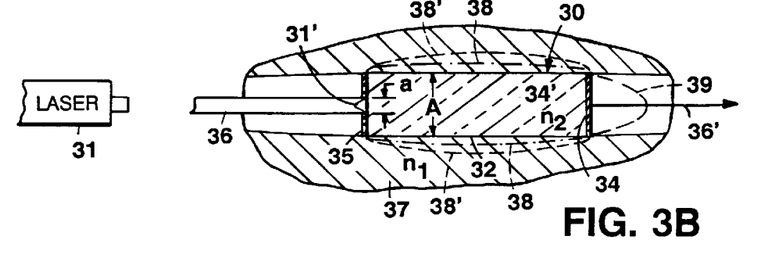
FIG. 3B is a schematic of a device as in FIG. 3A, but including a distal aperture that additionally provides forward-cutting by a portion of the laser energy.

As shown in FIG. 3B, the tip may also be designed to emit some of the light as a conventional beam 36' through an aperture 34' in distal mirror 34. In such a design, blunt tip 39 would be transparent to the laser beam or would be provided with an aperture or window through which the beam could pass. This design combines the forward-cutting ability of present optical catheters with the controlled side-ablating capacity of either the refracted or the evanescent waves.

In each embodiment, a conventional optical fiber 36 is used to deliver pulsed laser energy from a laser 31 of appropriate wavelength(s) into the optical resonator 30 constructed of a high refractive index material such as sapphire ($n_2=1.7$), with polished parallel end walls. For example, holmium or Q-switched holmium lasers, or other lasers in the 1.7 to 2.2 µm wavelength region, or pulsed dye lasers in the visible spectrum may be used. The tissue 37' ($n_1=1.35$ to 1.38) must contact the resonator 30 to create interface 32 across which the desired waves are generated. In this example using a sapphire resonator, the critical angle, $\theta_c$, is arcsin 1.35/1.7, about 52.60.

The angle of the laser energy entering the resonator can be set by appropriate selection of the prism angle of prism 31' which causes the entering energy to be refracted into the resonator. The efficiency of the resonator can be increased somewhat by increasing the ratio between the resonator cross-sectional area "A" and fiber cross-sectional area "a". The parallel polished ends of the resonator 30 are coated with conventional maximum-reflective all-dielectric mirrors 34, 35 such that photons bounce many times between the ends, greatly increasing the number of encounters with the tissue interface 32, which extends along the polished walls of the resonator. In this configuration, essentially no energy escapes from the distal end of the resonator 30, and a greatly intensified wave of the desired type propagates just outside the wall of the resonator to the desired penetration depth 38, 38'.

Figure 3C:
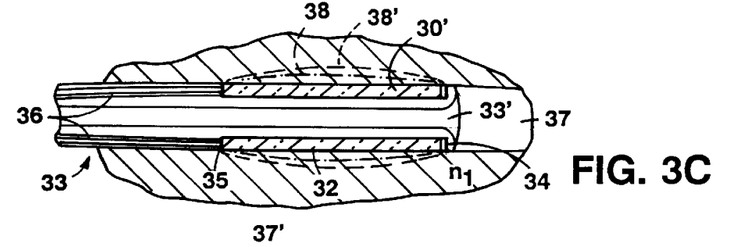
FIG. 3C is a schematic of a wave generator including a lumen for a guide wire.

Another embodiment of this optical resonator is shown in FIG. 3C, in which the resonator 30' is in the form of a hollow cylinder inserted in the wall of catheter 33 with a lumen 33' to allow the insertion and direction of the catheter over a guide wire (not shown). The resonator 30' has a mirrored, e.g., all-dielectric reflective coated distal end 34, and is coupled to a hollow cylinder 30' containing optical fibers 36, e.g., each fiber with a 50 to 200 µm diameter, via a proximal anti-reflection coated surface 35. The optical fibers 36 are inserted between inner and outer walls of catheter 33. As in FIG. 3A, the catheter 33 is inserted into a blood vessel 37 in tissue 37' with a refractive index $n_1$. Laser energy is introduced into the resonator 30' via the optical fibers 36 and creates a refracted wave field to a depth of about 20 µm when a holmium laser is used with a refracted wave resonator and the angle of refraction, $\theta_r$, equal to 85° as indicated by the dashed line 38', or an evanescent wave field to a depth of about one wavelength or less, as indicated by the dashed-dotted line 38, across tissue interface 32. The advantages of this embodiment include greater flexibility and guide wire compatibility.

The waves generated by each of these embodiments provide extremely localized tissue ablation depth per pulse of laser energy, e.g., 20 µm for refracted waves and a few µm for evanescent waves, over the large, uniform, smooth cylindrical surface of the resonator. As the tissue must contact the resonator to be ablated, the lumen produced will conform to the resonator shape and outer diameter. The debris produced by pulsed laser ablation varies generally in size with the absorption depth of the energy within the tissue 37'; hence, the debris size will be on the few-µm scale as opposed to the hundreds-of-µm scale typical for conventional ablation of tissue with fiber-compatible wavelengths (about 300 to 2500 nm). Thus, the major problems associated with fiber-compatible wavelengths when used for selective pulsed laser ablation of atherosclerotic plaques, for example, large debris particle size and excessive photomechanical injury, are avoided when these same wavelengths are used in the resonator according to the invention. By efficiently creating the desired refracted or evanescent wave, this or similar optical resonators make it possible for fiber-compatible laser wavelength radiation that would otherwise create gross damage, e.g., holmium or Q-switched holmium laser radiation, to be used safely.

The use of blue visible radiation pulses is desirable for removal of atherosclerotic plaque with the catheter devices as described above, because of the ablation selectivity of this type of radiation. Prince et al., *Proc. Natl. Acad. Sci.*, 83:7064–7068 (1986).

Corneal Laser Ablation Devices

The concepts of the invention also can be used for corneal refractive laser surgery. Refracted or evanescent optical waves can be used to ablate a cornea to a precisely predetermined and conventional optically correct surface shape with minimal thermal injury using lasers that are simpler and more reliable than the 193 nm excimer laser systems typically used for corneal ablation.

Figure 4A:
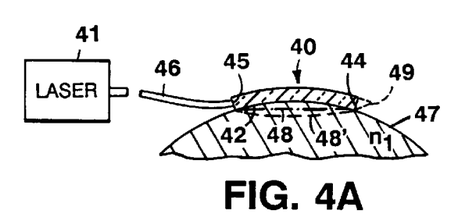
FIG. 4A is a schematic of a wave generator for corneal ablation.

As shown in FIG. 4A, a fused silica, glass, silicon, germanium, or sapphire contact lens 40 is used as the optical generator or resonator. This resonator lens may be constructed by conventional optical grinding and polishing or other means, and is used to create and propagate the desired optical waves across an interface 42 into the superficial layers of the cornea 47 to a depth of about 20 µm when a holmium laser is used with a refracted wave resonator and the angle of refraction, $\theta_r$, equal to 85° as indicated by the dashed line 48' or an evanescent wave field to a depth of about one wavelength or less, as indicated by dashed-dotted line 48. As lens 40 is gently advanced into the cornea 47, ablation occurs and material is removed. The resulting ablation is limited to tissue ($n_1 \approx 1.35$) which is within a few µm of the surface of the contact lens, and hence the outer shape of the cornea becomes a precise replica of the contact lens/tissue interface.

As in the resonator described above, an optical fiber 46 delivers laser energy from a laser 41 to the resonator lens 40. The laser energy enters the proximal end 45 of the lens and is reflected by the polished end wall 44 of the lens unless it strikes the bottom wall that forms the interface 42 with the corneal tissue 47 ($n_1$ being less than the refractive index $n_2$ of the lens) at an angle less than the critical angle, in which case refracted waves are generated in the tissue, or at an angle greater than or equal to the critical angle, in which case evanescent waves are generated in the tissue. The distal end of the lens may be coated with a reflective material, or it may be provided with a corner reflector 49 (as shown by the dashed lines). The proximal end of the resonator lens also may be coated with a reflective material as described above.

Figure 4B:
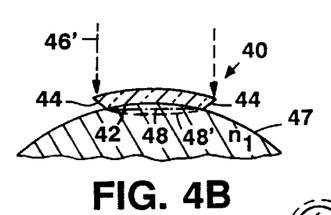
FIG. 4B is a schematic of a wave generator as in FIG. 4A, but not employing an optical fiber.
Figure 4C:
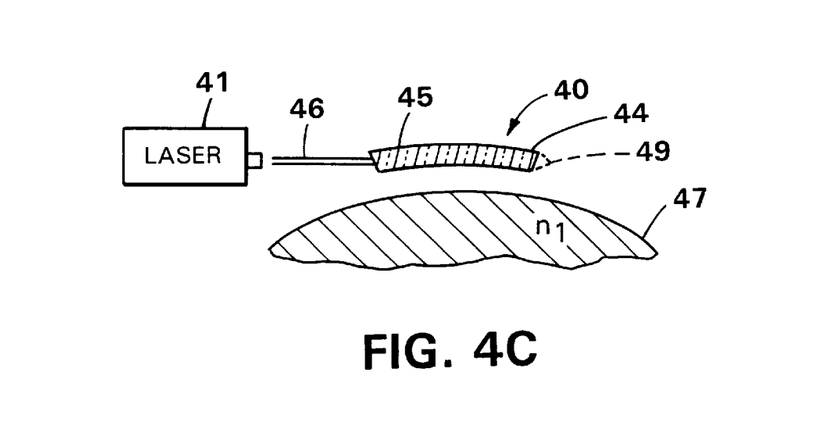
FIG. 4C is a schematic of the wave generator of FIG. 4A, showing the wave generator before contacting the cornea.

Another design of the wave generator lens does not use fiber optics. As shown in FIG. 4B, laser beam 46' is coupled directly into the edge of the device 40, which in this case need not be a resonator. The annular laser beam 46' is coupled into the wave-generating contact device 40 such that the angle of incidence at the device-cornea interface 42 is less than critical angle $\theta_c$ for generating refracted waves, and greater than or equal to the critical angle $\theta_c$ for generating evanescent waves. The convex and concave surfaces are very nearly arc-parallel, such that the incident angle is held nearly constant for multiple internal reflections.

For greater coupling efficiency into the device, a polarized laser can be used and is arranged to enter the device at or near Brewster's angle. At Brewster's angle, there is no loss from reflection of polarized light entering the device, and the coupling efficiency between either the refracted or evanescent wave-generating device and the tissue is also increased. The ablation effect is otherwise the same as in the optical resonator shown in FIG. 4A and described above.

Human Stratum Corneum Removal Device

Removal of human stratum corneum for drug delivery should be possible using either the refracted or the evanescent wave resonators of the invention that are much simpler than existing excimer laser systems. According to one embodiment of the invention, using lasers other than the conventional strongly-absorbed excimer laser systems, a device can be constructed in much the same way as the corneal sculpting laser ablation contact lens described above. In particular, a laser, such as a diode-pumped solid state holmium microchip laser, may be used to produce results that are the same or similar to those of the excimer laser system. These lasers are small, portable, and can even be battery-powered, with high reliability and long life. Thus, the device makes it possible to apply a highly desirable, but otherwise inapplicable, laser for this application.

The device is similar to that for corneal sculpting as shown in FIGS. 4A and 4B, but does not require a highly precise shape at the interface. It is therefore simpler. The preferred configuration is a near-planar surface from which the refracted or evanescent wave is propagated into the stratum corneum. It is also desirable to have a somewhat higher refractive index for the resonator lens. Sapphire ($n_2=1.7$) or germanium ($n_2=4$) are preferred materials to establish the necessary index mismatch to the tissue, since stratum corneum has an especially high refractive index ($n_1=1.55$) due to its reduced water content. The preferred combination is the use of a silicon or germanium resonator, or other high refractive index material, with a small holmium or erbium laser.

Endodontal Root Canal and Dental Laser Ablation Devices

Figure 5A:
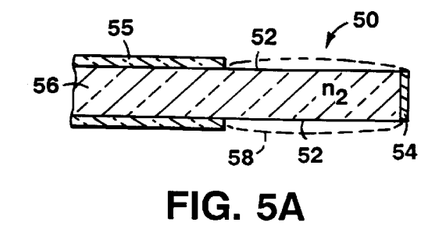
FIG. 5A is a schematic of a wave generator for dental applications.

Endodontal root canal and caries removal procedures present conceptually similar problems, i.e., the interaction depth and thermal injury must be limited, and the ablation shape should be controlled by contact with the device, or copying of the device diameter. According to the invention, the use of both refracted and evanescent wave energy is also suitable for these dental applications. The use of either refracted or evanescent wave propagation allows tooth-cutting laser pulses that are fiber optic-compatible, but would otherwise cause unacceptable thermal damage when used as a free beam. It is a straightforward task for one skilled in this field to create a narrow, side-ablating resonator 50, as shown in FIG. 5A, for, e.g., root canal operations, by utilizing the descriptions of other resonators made above.

For example, an optical fiber or a rod 56, e.g., of diamond-coated sapphire, with a refractive index $n_2$ of about 1.5 to 1.7, may be covered by a conventional cladding 55 except for its distal end to create an operative zone 58 where the desired waves can form when the fiber is held against a tooth surface. The refractive index $n_1$ of the tooth is estimated to be about 1.4. The polished distal end wall of the fiber may be coated with maximum-reflective dielectric mirror 54, such that photons are reflected to increase the number of encounters with the tooth interface 52, which extends along the walls of the resonator 50 in the non-clad zone 58.

A secondary advantage of this device is that the system offers the tactile feedback and physical manipulation ability that dentists rely on for their operations.

Figure 5B:
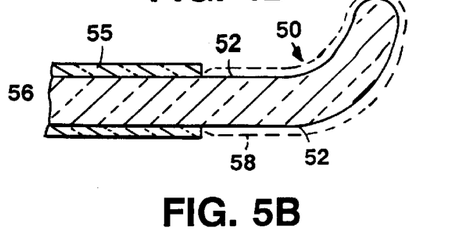
FIG. 5B is a schematic of a wave generator similar to that shown in FIG. 5A, showing a different shape.

For tooth ablation in caries removal and reconstruction, an undermined opening is needed prior to placement of filling or restorational materials. The device shown in FIG. 5B illustrates the adaptability of the invention to different generator or resonator shapes, still capable of producing the desired wave energy on the tip and sides of the device. As in FIG. 5A, the optical fiber or rod 56, e.g., of sapphire, is covered by a conventional cladding 55 except for its curved distal end to create an operative zone 58, shown by dashed lines, where the desired waves can form when the fiber is held against a tooth surface.

Laser Lithotripsy Devices

Laser lithotripsy devices can be designed to ablate kidney stones, gall stones, and similar concretions. Such stones are mostly calcium salts having a refractive index of at least 1.4. Using a mechanically tough resonator, e.g., diamond or diamond coated sapphire, that would not be destroyed by the plasma and shock waves created during stone fragmentation, laser energy can be coupled into such stones using either a refracted or evanescent wave generator. A refracted wave generator can be constructed to couple energy into a material with a higher refractive index, e.g., stone, and not into a material with a lower refractive index, e.g., renal tissue, saline, or bodily fluids. The resonator shape is not critical because during stone ablation it is not desired to create a specified shape in the substrate.

Lasers and Apparatus

In preferred embodiments, three different pulsed laser systems are preferred for superficial alteration, e.g., ablation or photochemical alteration, of a substrate. Other lasers can be used as long as the proper wavelengths and pulse-widths are achieved as described above. Each laser described below has different advantages.

Pulsed $CO_2$ lasers, for example "superpulsed" $CO_2$ surgical lasers, or very powerful transverse excited atmospheric (TEA) $CO_2$ lasers having a 0.2 $\mu$s pulse-width and up to 2 J per pulse at 10.6 $\mu$m multiline output, e.g., those manufactured by Lumonics, London, England, are capable of generating ablation of tissue from evanescent or refracted wave absorption.

Normal-mode pulsed holmium lasers, e.g., a Model 123, manufactured by SEO, Inc., Concord, Mass., and short-pulsed holmium lasers (0.5 to 10 $\mu$s, 2 $\mu$m), e.g., a cryogenic holmium/thulium laser, manufactured by Rare Earth, Inc., Dennis, Mass., are useful for refracted wave and evanescent wave ablation, respectively.

Flashlamp-pumped tunable dye lasers operating in the visible spectrum, e.g., those manufactured by Candela Laser Corporation, Wayland, Mass., in which the laser pulse duration can be varied between 0.3 and 10 $\mu$s at wavelengths where the absorption coefficient, $\mu_a$, can be varied from 10 to 1000 $cm^{-1}$, can also be used. This laser facilitates the choice of wavelength, the determination of pulse duration effects, and the control over the early events of cavitation-induced energy decoupling.

Each laser is coupled via a collimated beam of 1 to 5 mm diameter with a spatial beam intensity distribution as close to flat as possible, to prisms in which the incident angle can be varied by simply changing alignment relative to the incoming beam. A Ge prism or resonator type wave generator is used with the $CO_2$ laser. Fused silica, a sapphire prism, or a resonator type wave generator is used with the holmium and tunable dye lasers. Wave generators made with silicon are appropriate for use with the holmium laser and others operating near the 2 $\mu$m wavelength.

A wave generator or resonator designed according to the parameters described herein can be tested on biological tissue in vitro using routine procedures, e.g., by gradually increasing laser energy intensity coupled into the wave generator until ablation is visually observed. The tissue can then be analyzed, e.g., microscopically, to ensure that the desired penetration depth has been achieved. The penetration depth and energy intensity required for ablation can then be adjusted according to the equations described above.

Other embodiments are within the following claims.

What is claimed is:

1. A method of altering a substrate having a first refractive index and an absorption coefficient $\mu_a$, said method comprising:

contacting a solid optical coupler to the substrate to form an interface with the substrate, said optical coupler having a second refractive index higher than said first refractive index, selecting a desired penetration depth ($\delta_r$) of laser energy into said substrate that is less than $1/\mu_a$, and setting an angle of refraction ($\theta_r$) of said laser energy into said substrate at said interface to produce the desired penetration depth ($\delta_r$) according to the equation $\delta_r \approx (1/\mu_a) \cos \theta_r$.

2. The method of claim 1, wherein said optical coupler is provided with a refractive index of at least about 1.7.

3. The method of claim 1, further comprising providing the laser energy from a holmium laser, a $CO_2$ laser, a dye laser, an erbium laser, or a thulium laser.

4. The method of claim 1, further comprising providing the laser energy as pulsed laser energy at a wavelength of 1.7 to 2.2 microns.

5. The method of claim 1, further comprising providing the laser energy as pulsed laser energy at a wavelength of 2.7 to 3.2 microns.

6. The method of claim 1, further comprising providing the laser energy as pulsed laser energy at a wavelength of 10.6 microns.

7. The method of claim 1, further comprising providing the laser energy as pulsed laser energy at a wavelength of 420 to 510 nm.

8. The method of claim 1, further coupling the laser energy into the optical coupler via an optical fiber.

9. The method of claim 1, wherein the substrate contacted by the optical coupler is biological tissue.

10. The method of claim 9, wherein the biological tissue is atherosclerotic plaque.

11. The method of claim 9, wherein the biological tissue is stratum corneum.

12. The method of claim 9, wherein the biological tissue is corneal tissue.

13. The method of claim 9, wherein the biological tissue is concretion.

14. The method of claim 9, wherein the biological tissue is tooth enamel.

15. The method of claim 9, wherein the biological tissue is dentin.

* * * * *